United States Patent
Andrews et al.

(10) Patent No.: US 9,759,830 B2
(45) Date of Patent: Sep. 12, 2017

(54) METHOD AND APPARATUS FOR DETERMINING MUD CONTAMINATION OF FORMATION FLUID

(71) Applicant: SCHLUMBERGER TECHNOLOGY CORPORATION, Sugar Land, TX (US)

(72) Inventors: A. Ballard Andrews, Wilton, CT (US); Soraya S. Betancourt, Katy, TX (US); Andrew E. Pomerantz, Lexinton, MA (US); Soumyajit Mandal, Cambridge, MA (US); Yi-Qiao Song, Newton, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 800 days.

(21) Appl. No.: 14/067,475

(22) Filed: Oct. 30, 2013

(65) Prior Publication Data

US 2015/0115953 A1    Apr. 30, 2015

(51) Int. Cl.
| | | |
|---|---|---|
| G01V 3/08 | (2006.01) | |
| E21B 49/00 | (2006.01) | |
| G01N 24/08 | (2006.01) | |
| G01V 3/32 | (2006.01) | |

(52) U.S. Cl.
CPC ............ *G01V 3/08* (2013.01); *G01N 24/081* (2013.01); *G01V 3/32* (2013.01)

(58) Field of Classification Search
CPC ........ G01N 24/08–24/088; G01V 3/08; G01V 3/32; E21B 49/00–49/10
USPC ....................................................... 324/303
See application file for complete search history.

(56) References Cited

U.S. PATENT DOCUMENTS

| | | | | |
|---|---|---|---|---|
| 5,962,604 A | * | 10/1999 | Rath ..................... | C08F 110/10 585/521 |
| 6,051,639 A | * | 4/2000 | Mehl ..................... | C08G 77/38 524/205 |
| 7,271,231 B2 | * | 9/2007 | Brookhart ............. | C08F 210/02 526/161 |
| 7,637,151 B2 | * | 12/2009 | Raghuraman ...... | G01N 33/2823 250/255 |
| 7,880,047 B2 | * | 2/2011 | Knowles ................. | C08F 10/14 585/521 |
| 8,248,067 B2 | * | 8/2012 | Ong ..................... | G01N 24/081 324/303 |

(Continued)

OTHER PUBLICATIONS

Joseph a Curiale et al., Occurrence and Origin of Olefins in Crude Oils. A Critical Review., Organic Chemistry, 1998, pp. 397-408, vol. 29, Nos. 1-3.

*Primary Examiner* — Melissa Koval
*Assistant Examiner* — Rahul Maini
(74) *Attorney, Agent, or Firm* — Bridget Laffey

(57) ABSTRACT

A formation fluid sample is analyzed using NMR spectroscopy to obtain a NMR spectrum. The NMR spectrum is then analyzed to find evidence of the amount of olefins present in the sample. The amount of olefins present in the sample can then be correlated to the level of contamination of the sample. In one embodiment, a $^1$H chemical shift of between substantially 4.5 and 6 ppm is used to identify olefins present in the sample. In another embodiment, a $^1$H chemical shift of substantially 1.9 to 2.1 ppm is used to identify olefins present in the sample. The NMR spectral equipment can be located uphole or downhole.

24 Claims, 6 Drawing Sheets

(56) References Cited

U.S. PATENT DOCUMENTS

| | | |
|---|---|---|
| 8,471,559 B2 | 6/2013 | Taherian et al. |
| 8,735,521 B2 * | 5/2014 | Sung .................... C08F 210/02 |
| | | 526/161 |
| 9,334,727 B2 * | 5/2016 | Jones .................... E21B 49/005 |
| 2012/0169334 A1 | 7/2012 | Hopper et al. |
| 2014/0225607 A1 * | 8/2014 | Edwards ............. G01N 24/081 |
| | | 324/303 |

* cited by examiner

METHOD AND APPARATUS FOR DETERMINING MUD CONTAMINATION OF FORMATION FLUID

FIELD

The subject disclosure relates to the oilfield. The subject disclosure more particularly relates to nuclear magnetic resonance (NMR) methods and apparatuses for determining mud contamination of a formation fluid.

BACKGROUND

Wellbores are drilled in geological formations using a drill rig supporting a drill bit. In order to help in the drilling, drilling mud is circulated from the surface of the formation to the drill bit, and the mud with the cuttings from the formation is brought to the surface for disposal. The drilling mud can be a water based mud, an oil based mud (OBM), or a synthetic based mud (SBM). After the wellbore has been drilled it is common for mudcake to line the wellbore.

In determining the nature of the fluid (oil) in the formation for purposes of producing oil, it is common to place tools into the wellbore and against the formation to obtain formation fluid samples. For example, the Modular Formation Dynamics Tester™ (MDT) tool of Schlumberger may be used to collect formation fluid samples and bring them to the surface for laboratory analysis. The MDT tool is located in the wellbore and a pressure seal is made with the formation reservoir via a retractable hydraulically activated probe head. Onboard pumps then draw fluid into a flow line inside the tool body. Often, upon initial drawing of fluid into the flow line, the reservoir fluids are contaminated by the drilling fluids (e.g., OBM or SBM) mixed with the mud. To ensure that the samples collected have low levels of contamination, an optical port is placed in the flow line and the fluid is monitored using near infrared (NIR) spectroscopy. Nonetheless, samples are sometimes brought to the surface with high levels of drilling fluid contamination. This can happen when there is formation water that is mixed by the action of the pumps and forms a stable emulsion. The scatter from the emulsion water droplets compromises the absorption measurement and the samples are collected blindly, so there is a reasonable probability that an unacceptably high contamination level will exist. This can also happen when the near infrared spectral fingerprint of the oil in the drilling fluid overlaps the near infrared spectral fingerprint of the formation oil. Regardless, collection and use of contaminated samples is not desirable as it may lead to incorrect analysis of the formation fluid resulting in less than optimal determinations regarding production.

The standard laboratory technique for determining contamination levels is through use of a gas chromatography (GC) subtraction method. In this method, components of the sampled fluid are separated according to GC retention time. In favorable cases, peaks in the GC chromatogram resulting from investigation of the drilling fluid can be resolved, identified and quantified, and then the level of contamination can be estimated by comparing the intensity of the drilling fluid peak with the intensity of an internal standard. However, this method suffers when components of the drilling fluid cannot be separated from components of the petroleum by GC, as is common in heavy oils, biodegraded oils, or water washed oils.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one embodiment, a $^1$H proton NMR spectrum is obtained of a formation fluid sample. The spectrum is analyzed to find evidence of a concentration of olefins present in the sample. The concentration of olefins present in the sample can then be correlated to the level of contamination of the formation fluid sample. In another embodiment a $^{13}$C NMR spectrum is obtained of the sample, and the spectrum is analyzed to find evidence of the concentration of olefins present in the sample which may be correlated to the level of contamination of the sample.

In one embodiment, for the $^1$H proton NMR spectrum, a chemical shift in the proton spectrum of between substantially 4.5 and 6 ppm is used to identify olefins present in the sample. In another embodiment, a chemical shift of substantially 1.9 to 2.1 ppm is used to identify olefins present in the sample. In another embodiment, for the $^{13}$C NMR spectrum, a chemical shift of between substantially 114 and 115 and/or between substantially 125 and 140 ppm (e.g., between substantially 131 and 140 ppm) is used to identify olefins present in the sample. In yet another embodiment, a $^{13}$C spectrum chemical shift of between substantially 34 and 40 ppm (e.g., between substantially 39 and 40 ppm) is used identify olefins present in the sample.

In one embodiment, the concentration of olefins present in the sample is found by integrating under the peaks in a particular area of the spectrum and dividing that by the area under all peaks in the spectrum. In another embodiment, a known amount of an internal standard is added to the sample, and the amount of olefins present in the sample is found by integrating under the peaks in a particular area of the spectrum and dividing by the area under the peak of the internal standard. For the $^1$H proton NMR spectrum, the particular area of the spectrum used to quantify the amount of olefins may be between 4.5 and 6 ppm and/or between 1.9 to 2.1 ppm. For the $^{13}$C NMR spectrum, the particular area of the spectrum used to quantify the amount of olefins may be between substantially 114 and 115 and/or between substantially 125 and 140 ppm (e.g., between substantially 131 and 140 ppm). In yet another embodiment, for the $^{13}$C NMR spectrum, the particular area of the spectrum used to quantify the amount of olefins may be between substantially 34 and 40 ppm (e.g., between substantially 39 and 40 ppm).

DETAILED DESCRIPTION

Illustrative embodiments of the present disclosure are directed to methods and tools for determining a concentration of synthetic based drilling mud contamination in formation fluids using a nuclear magnetic resonance (NMR) spectrum. A synthetic based drilling mud (SBM) is defined herein as a drilling mud that includes olefins. In turn, an olefin is defined herein as a cyclic or acyclic unsaturated chemical compound that includes at least one unconjugated carbon-carbon double bond. Typical base fluids that are used in synthetic based mud are linear monoolefins, polyalphaolephins (PAOs), linear alphaolephins (LAOS) and/or internal/isomerized olefins (IOs). As explained above, drilling muds are used to facilitate drilling of a wellbore. Synthetic based drilling muds are often used instead of oil based muds (OBM) because the olefins of the base fluids in synthetic based muds are generally unstable and will readily break down into non-toxic components. Nonetheless, synthetic based mud contamination can adversely impact a compositional analysis of formation fluid. Thus, the concentration of synthetic based mud contamination within the formation fluid sample is valuable information that can be used to ensure analysis of formation fluids with low levels of contamination. Details of various embodiments are discussed below.

A concentration of synthetic based drilling mud (SBM) contamination in formation fluid is defined herein as an amount of a SBM in relation to some or all other chemical components within the formation fluid. The concentration of SBM contamination can be a fraction or a percent, such as a weight percentage, a molar percentage, and/or a volume percentage. Furthermore, the concentration of SBM contamination in formation fluid may be (i) a relative amount of some or all components of the SBM within the formation fluid, (ii) a relative amount of one or more olefins of the SBM within the formation fluid, (iii) and/or a relative amount of one or more nuclei of olefins within the formation fluid (e.g., a hydrogen weight percentage of the olefins).

Figure 1:
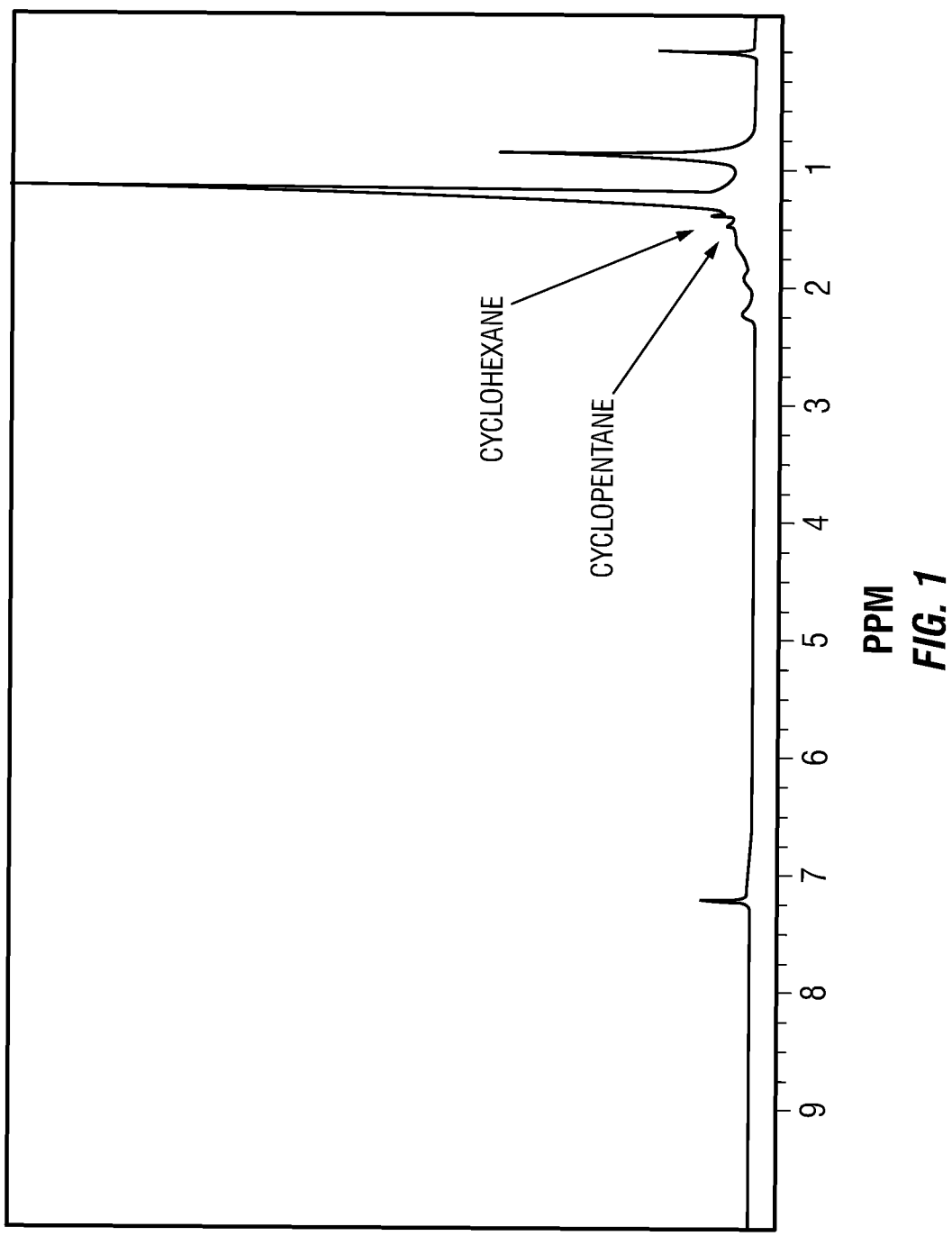
FIG. 1 shows a complete $^1$H proton NMR spectrum of a typical crude oil sample with a relatively high level of synthetic based mud contamination.
Figure 2:
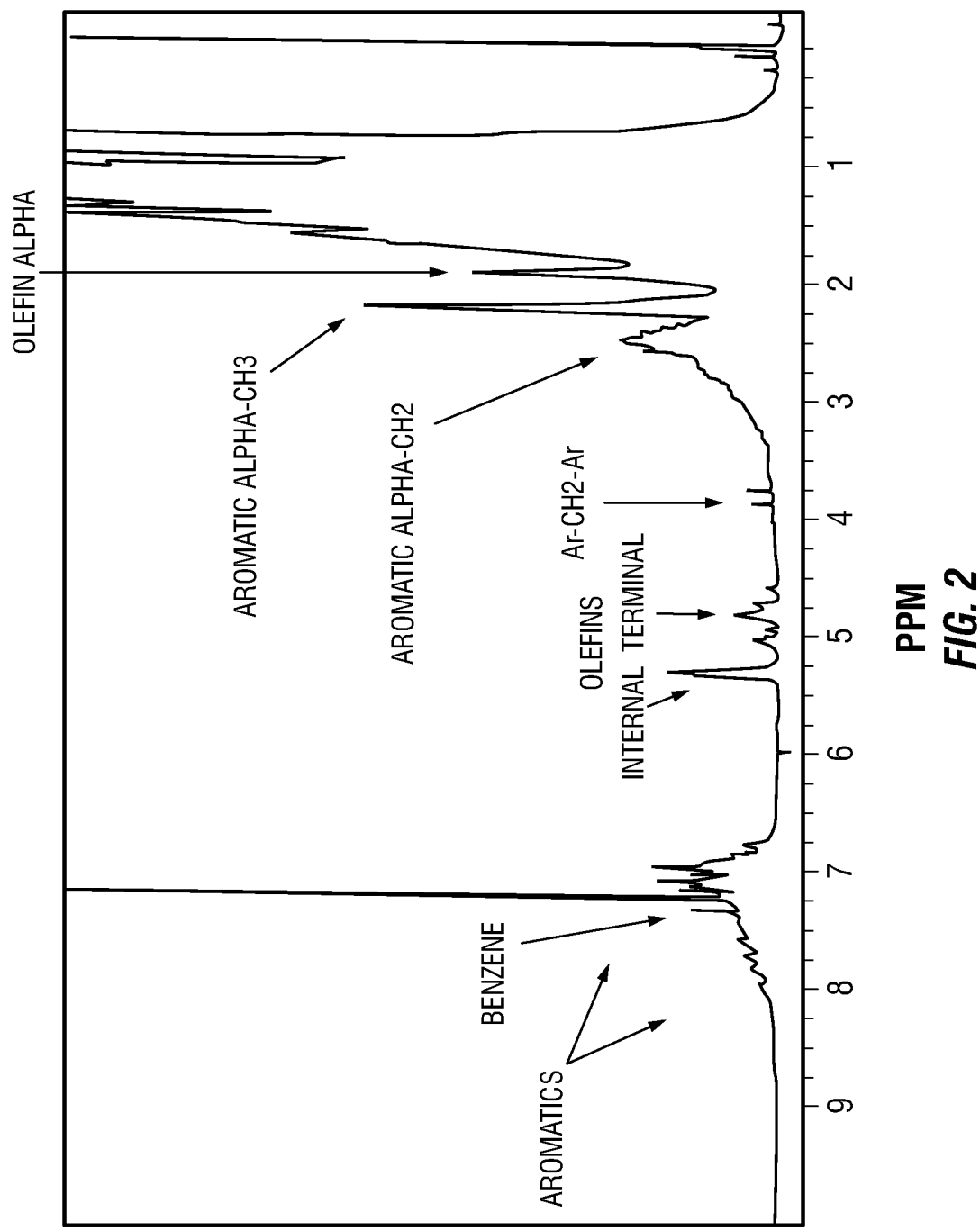
FIG. 2 shows the spectrum of FIG. 1 with a different scale that gives emphasis to the olefin peaks.

FIGS. 1 and 2 (FIG. 2 showing FIG. 1 with a different scale in order to highlight the peaks) show a $^1$H proton NMR spectrum of a formation fluid with a relatively high level of synthetic based mud contamination (12.3% concentration as measured by gas chromatography). In this case, the formation fluid is a typical crude oil sample. The spectrum, shown as a function of spectral shift in parts per million (ppm), is obtained by subjecting the sample to a NMR pulse sequence and acquiring spectral information with a NMR apparatus, as is known in the art. In FIGS. 1 and 2, the peaks of various constituent groups of the crude oil sample are labeled, such as the aromatic group (e.g., benzene in FIG. 2) and the aliphatic group (cyclopentane in FIG. 1, cyclohexane in FIG. 1, alpha-CH$_3$ in FIG. 2, and alpha-CH$_2$ in FIG. 2). Also shown and labeled in FIG. 2 are the olefins. The olefins are rarely found in crude oil and thus are assumed to come from the SBM contamination.

As seen in FIG. 2, the spectral shifts of the olefins do not overlap with the spectral shifts of the aromatic or aliphatic regions of the $^1$H proton NMR spectrum, allowing the level of contamination to be accurately determined by integration as discussed hereinafter. The internal and terminal olefins are clearly distinguished in the spectrum, and the peaks can be integrated to yield a concentration (e.g. ratio) of synthetic based mud (SBM) to crude oil. In addition, an "olefin alpha" which is an aliphatic compound adjacent an olefin is seen in FIG. 2. Although not directly representing an olefin, the olefin alpha peak will occur when olefins are present in the sample, and therefore indirectly indicate the presence of an olefin.

As previously suggested, it is possible to take an integral of the signal under a peak representing a compound in order to determine the amount of any particular compound in the sample. The chemical shift boundaries for integration limits for aromatic, aliphatic, and olefin compounds may be set based on the peaks, or more generally as desired. For example, chemical shift boundaries are shown in Table 1.

TABLE 1

Chemical shifts and integration limits for aromatic and aliphatic protons:

| Proton NMR Regions | Begin (ppm) | End (ppm) |
|---|---|---|
| TMS | 0 | 0 |
| CH$_3$ | 0.5 | 1.0 |
| CH$_2$ - Long Chain | 1.0 | 1.4 |
| CH/CH$_2$ Isoparaffins and Napthenes | 1.4 | 2.0 |
| Alpha-H All Types | 2.0 | 3.0 |
| Hetero - H (O + S) and Ph-CH$_2$-Ph | 3.0 | 4.5 |
| Olefin H | 4.5 | 6.0 |
| Mono-Aromatic H | 6.0 | 7.2 |
| Di-Aromatic H | 7.2 | 7.8 |
| PNA2 - Di + Tri Aromatic H | 7.8 | 8.2 |
| PNA1 - Tri + Tetra + Aromatic H | 8.2 | 9.3 |
| CHC$_{13}$ Solvent | 7.24 | 7.24 |

In Table 1, the aliphatic group is broken into five subgroups: CH$_3$ between 0.5 and 1.0 ppm, CH$_2$-long chain between 1.0 and 1.4 ppm, CH/CH$_2$ isoparaffins and napthenes between 1.4 and 2.0 ppm, alpha-H between 2 and 3 ppm, and hetero-H between 3 and 4.5 ppm. Also, in Table 1 the olefin group is lumped together between 4.5 and 6.0 ppm. Further, the aromatic group is broken into four subgroups; Mono-Aromatic H between 6 and 7.2 ppm, Di-Aromatic H between 7.2 and 7.8 ppm, PNA2 (also called HeteroAromatic-H between 7.8 and 8.2 ppm, and PNA1 (also called TriAromatic-H) between 8.2 and 9.3 ppm. The tetramethylsilane (TMS) standard is the large signal set by definition at 0 ppm, and CHC$_{13}$ solvent is the large signal at 7.24 ppm.

Figure 3:
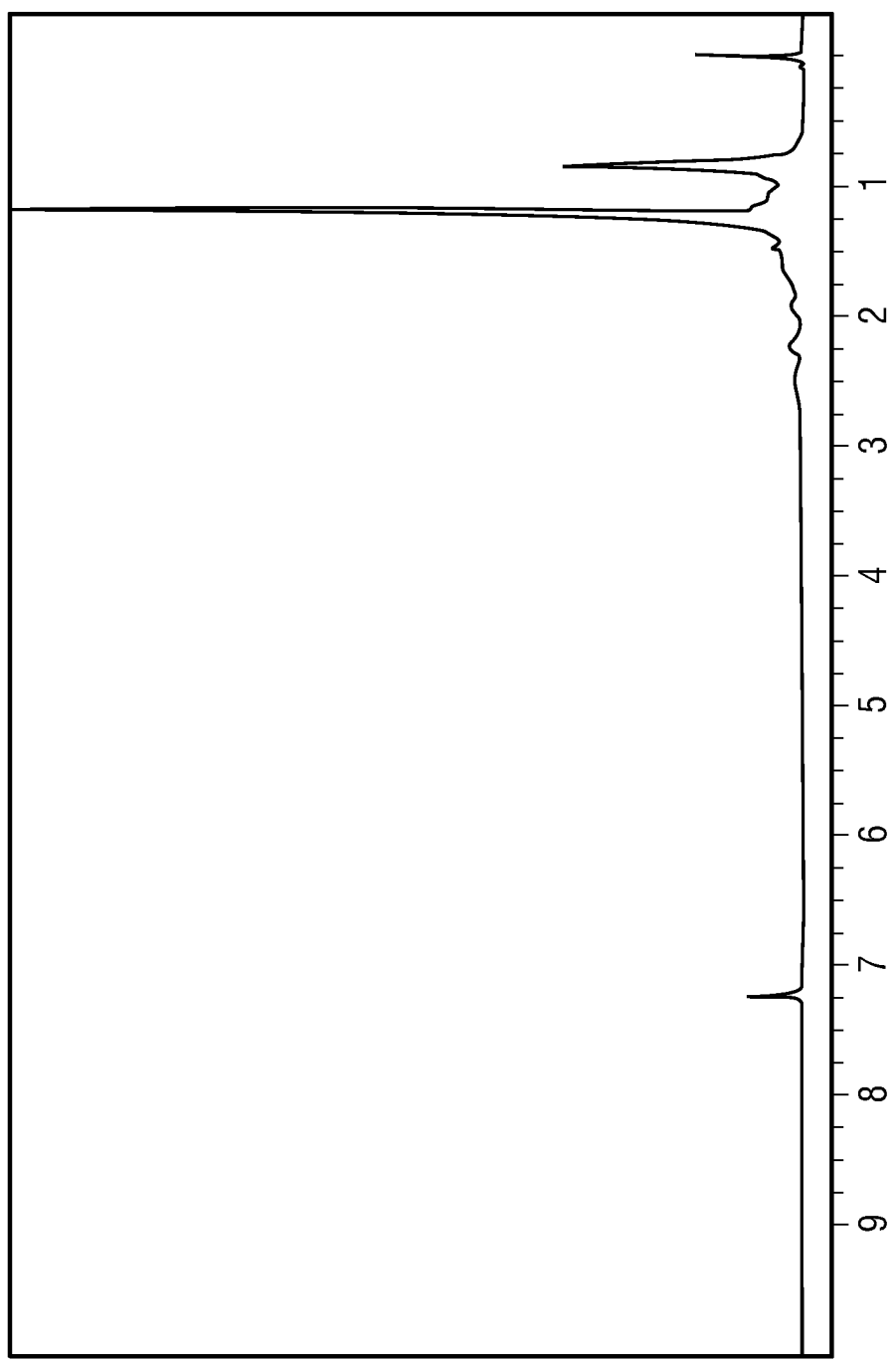
FIG. 3 shows a complete $^1$H proton NMR spectrum of a typical crude oil sample with a relatively low level of synthetic based mud contamination.
Figure 4:
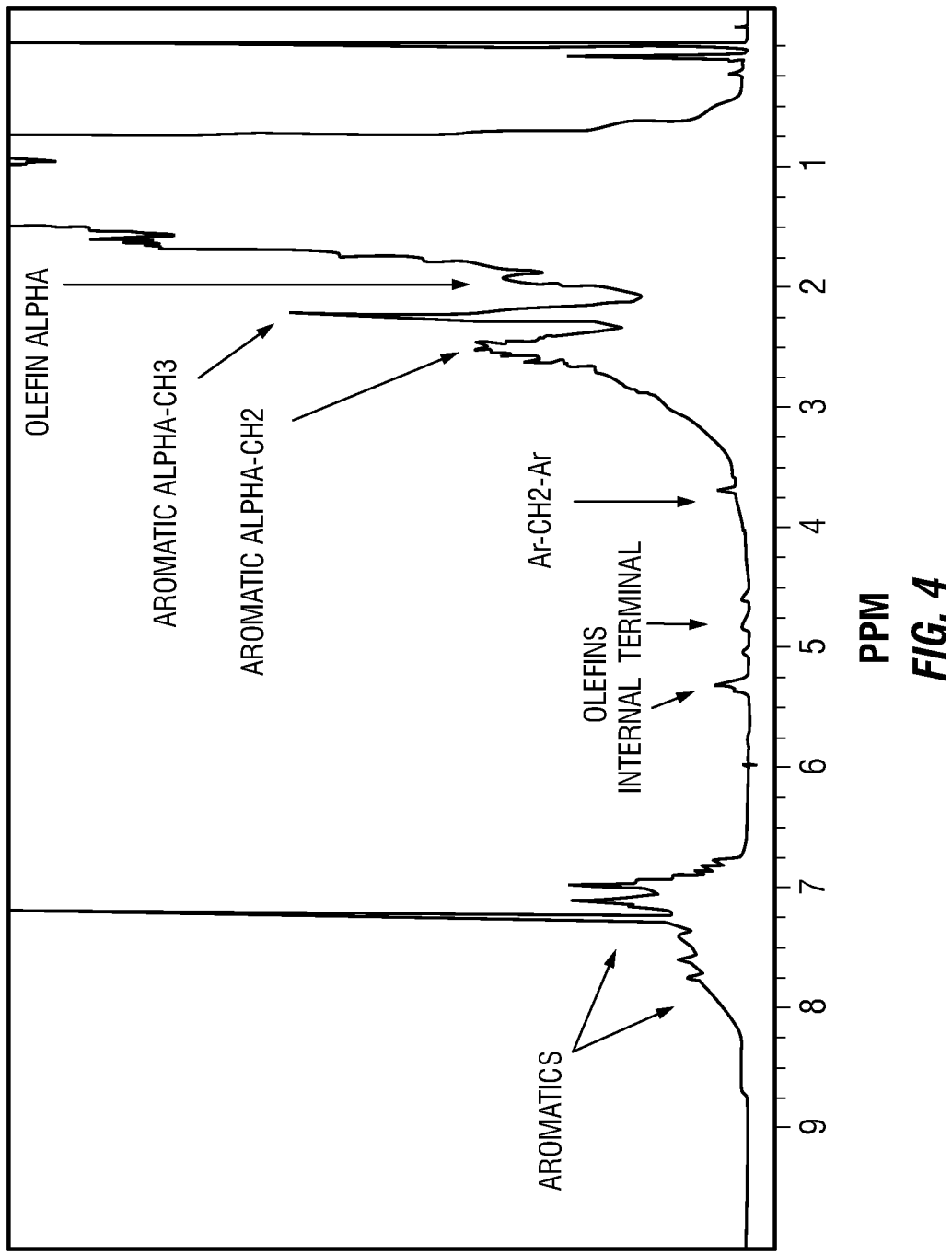
FIG. 4 shows the spectrum of FIG. 3 with a different scale that gives emphasis to the olefin peaks.

Turning now to FIGS. 3 and 4, the complete $^1$H proton NMR spectrum of a formation fluid with a relatively low level of SBM contamination (2.3% concentration as measured by gas chromatography) is seen with FIG. 4 showing the same spectrum as FIG. 3, but on a different scale to give emphasis to the olefin peaks. Again, in this case, the formation fluid is a typical crude oil sample. It will be appreciated that the spectra of FIGS. 3 and 4 are very similar to the spectra of FIGS. 1 and 2, but the olefin peaks, in particular, are much smaller than those of FIGS. 1 and 2.

The NMR spectra of FIGS. 1-2 and FIGS. 3-4 the NMR were analyzed (i.e., processed using integration) according to the chemical shifts and integration limits shown in Table 1 to produce quantitative determination of the compositions of the two samples. The quantitative determinations are shown in Table 2.

TABLE 2

$^1$H NMR results for High SBM (12.3%) and Low SBM (2.3%) samples:

| Sample Name | High | Low |
|---|---|---|
| Total Aliphatic-H | 95.6 | 95.2 |
| Total Olefinic-H | 0.6 | 0.1 |
| Total Aromatic-H | 3.8 | 4.7 |
| HeteroAromatic-H | 0.1 | 0.2 |

TABLE 2-continued

¹H NMR results for High SBM (12.3%) and Low SBM (2.3%) samples:

| Sample Name | High | Low |
|---|---|---|
| TriAromatic-H | 0.3 | 0.5 |
| DiAromatic-H | 1.2 | 1.5 |
| MonoAromatic-H | 2.2 | 2.5 |
| Alpha-H | 7.5 | 9.2 |
| $CH_2$ Alpha to 2 Aromatics | 0.3 | 0.4 |
| Alpha $CH_2$ | 4.9 | 6.3 |
| Alpha $CH_3$ | 2.3 | 2.5 |
| Beta-H | 62.3 | 61.2 |
| Beta $CH_2$ | 13.6 | 14.2 |
| Paraffinic $CH_2$ | 48.6 | 47 |
| Gamma-H | 25.9 | 24.7 |

In Table 2, the first three rows are respectively the hydrogen weight percentage totals of aliphatic, olefinic and aromatic compounds contained in the two different SBMs and total to 100%. The next four rows of Table 2 show a breakdown of the aromatic total into four distinct subgroups: heretero-, tri-, di- and mono-aromatics, with their totals equaling the total aromatic listed in the third row. The eighth row (alpha) is an aliphatic, and is broken down in the following three rows into three components ($CH_2$ alpha to 2 aromatics, alpha $CH_2$ and alpha $CH_3$). Similarly, the twelfth row (beta) is an aliphatic that is broken down in the following two rows into two components (beta $CH_2$ and paraffinic $CH_2$). The last row (gamma) is an aliphatic, and the gamma, beta and alpha aliphatics substantially total to the total aliphatic shown in the first row.

Particularly notable in comparing the "high" SBM column and "low" SBM column of Table 2 is that the total olefinic-H weight percentage (0.6%) in the sample with a high level of SBM contamination is substantially six times the total olefinic-H weight percentage (0.1%) in the sample with a low level of SBM contamination which correlates well with the gas chromatography determination that the high SBM sample contained 12.3% SBM, and the low SBM sample contained 2.3% SBM (a factor of 5.3). In addition, it is noted that the olefinic content of the SBM is approximately 5%-6%, with the remainder being aliphatic. Thus, where the sample contained approximately 12.3% SBM, it would be expected that the olefins would constitute approximately 0.6% of the sample (12.3%×0.05=0.615%) as was measured, and where the sample contained approximately 2.3%, it would be expected that the olefins would constitute approximately 0.1% of the sample (2.3%×0.05=0.115%).

In one embodiment, the hydrogen weight percentage of the olefins in a formation fluid is measured by integrating the area under the spectral olefinic NMR peaks and dividing that by the area under the NMR peaks of the spectrum (e.g., all of the NMR peaks of the spectrum). In another embodiment, the hydrogen weight percentage of the olefins in a formation fluid is measured by integrating the area under the spectral curve corresponding to a chemical shift of between 4.5 and 6 ppm and dividing that by the area under the entire spectral curve for hydrocarbons (e.g., 0.5 ppm to 9.3 ppm). According to another embodiment useful for most oil samples, but in particular for heavy oil samples, a known amount of a standard, such as tetramethylsilane (TMS) is added to the sample. After a spectral NMR experiment, the area under the olefin peaks or olefinic area (6.0 ppm to 4.5 ppm) is compared to the area under the TMS peak (at 0 ppm) in order to derive the hydrogen weight percentage of olefins in the sample. The total weight percentage of olefins may then be derived by knowing the hydrogen weight fraction of TMS and the hydrogen weight fraction of the SBM. It is noted that a standard other than or in addition to TMS may be utilized.

In one aspect, the weight percentage of the olefins may be converted to a weight percentage of the sample that is SBM by knowing the constituents of the SBM. Thus, by way of example only, if the olefins in the SBM are 5% by weight of the SMB, and olefins are 1.0% by weight of the sample, then the SBM is 20% by weight of the sample. Similarly, if the olefins in the SBM are 6% by weight of the SBM, and olefins are 0.2% by weight of the sample, then the SBM is 3% by weight of the sample.

It is noted with respect to the NMR measurements, that NMR measures the percentage of hydrogen (also called hydrogen weight percentage) attributable to the different groups. A weight percentage of a compound can then be inferred based on a knowledge of the hydrogen content of the SBM and of the oil, and of the standard, if one is used.

In one embodiment, a formation fluid (e.g., oil sample) obtained from a formation is obtained by a sample obtaining tool located in a wellbore (e.g., a wireline tool). The sample is brought uphole and subjected to an NMR spectral experiment (test). The concentration of contamination of the sample by SBM is then found by determining the olefinic content of the sample via the NMR spectral test and through knowledge or an estimate of olefinic weight percentage in the SBM.

In another embodiment, a formation fluid (e.g., oil sample) obtained from a formation is obtained by a sample obtaining tool located in a wellbore (e.g., a wireline tool). The sample is brought uphole, and TMS and/or another standard is added to the sample which is then subjected to an NMR spectral experiment (test). The concentration of contamination of the sample by SBM is then found by comparing the olefinic content of the sample via the NMR spectral test to the standard content and using that comparison as well as knowledge or an estimate of olefinic weight percentage in the SBM.

According to one aspect, an indication of the olefinic content of the formation fluid is used to estimate the concentration of SBM contamination of the sample. In one embodiment, the indication of the olefinic content is obtained by subjecting the sample to an NMR spectral test and inspecting the peaks in the 4.5 to 6.0 ppm portion of the spectrum. In another embodiment, the indication of the olefinic content is obtained by subjecting the sample to an NMR spectral test and inspecting the "olefin alpha" peak at approximately 1.9 to 2.1 ppm. While the olefin alpha peak is an aliphatic peak, it represents the amount of a particular aliphatic compound that is adjacent an olefin, thereby indicating the presence of an olefin. If a correlation is known for the area under this peak with the expected area under the olefinic peaks, then this peak can be used in lieu of the olefinic peaks in determining the olefinic content and hence the contamination. In one aspect, a correlation may be found by investigating numerous samples with different olefinic contents and comparing the area under the olefin alpha peak with the area under one or more of the olefinic peaks. In another embodiment, a correlation is found by comparing the area under the olefin alpha peak to the known olefin content of an SBM. The correlation can also be determined from the composition of the SBM.

The methods previously described may be conducted with NMR spectral equipment located uphole or downhole.

In another embodiment, rather than utilizing a ¹H proton NMR spectrum of a formation fluid (e.g., oil sample) in assessing whether or to what extent a formation fluid is contaminated with a SBM, a $^{13}$C NMR spectrum (carbon chemical shift) is obtained utilizing equipment located uphole or downhole and used to assess whether or to what extent a formation fluid is contaminated with a SBM. According to one aspect, by running a set of experiments on a number of different hydrocarbons, it can be determined that $^{13}$C chemical shifts are largely correlated to $^1$H proton chemical shifts. A correlation is shown in Table 3.

TABLE 3

Chemical shifts and integration limits for attached carbon atoms:

| Attached carbon atom | $^{13}$C chemical shift (ppm) | $^1$H chemical shift (ppm) |
| --- | --- | --- |
| Terminal, single-bonded (e.g., $CH_3$) | 14-17 | 0.9 |
| Adjacent to terminal, single-bonded | 22-23 | |
| Internal, single-bonded (e.g., $CH_2$) | 29-33 | 1.3 |
| Internal, adjacent to double-bonded (e.g., olefin-alpha) | 34-40 | 2 |
| Adjacent to aromatic | 21-38 | 2.0-2.3 |
| Terminal, double bonded (olefin) | 114-115 | 4.9-5.1 |
| Internal, double bonded (olefin) | 125-140 | 5.5-5.8 |
| Aromatic | 125-130 | 6.0-8.2 |

From Table 3, it can be seen that the presence of a $^{13}$C chemical shift signal at between substantially 114 and 115 ppm is indicative of the presence of a terminal double-bonded olefin that may be found in certain SBMs and is rarely found in crude oil. In addition, the presence of a chemical shift signal at between substantially 125 and 140 ppm may be indicative of the presence of an internal double-bonded olefin that may be found in an SBM and is rarely found in crude oil. However, because the $^{13}$C chemical shift of aromatics is at substantially 125-130 ppm, if there are aromatics in the sample, the presence of the aromatics can complicate a determination as to whether a signal relates to a terminal double-bonded olefin or not. Thus, in one embodiment, a chemical shift signal at between substantially 131 and 140 ppm is used to identify internal double-bonded olefins present in the sample.

Figure 5:
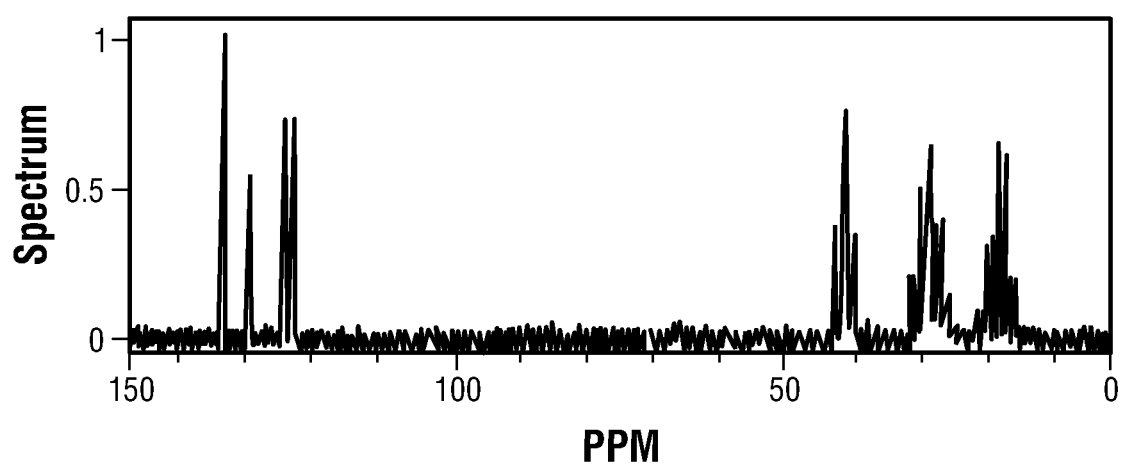
FIG. 5 shows a $^{13}$C NMR spectrum of squalene.

An example of an oil containing olefins that can be used in an SBM is squalene ($C_{30}H_{50}$) which is a natural hydrocarbon obtained from vegetable and shark liver oils. Squalene contains as many as six internal double bonds per molecule. As seen in FIG. 5, the carbon spectrum of squalene contains the three single-bond peaks as well as three double-bond peaks. The double-bond peaks are split apart because the molecule has methyl branches attached to one side of each double bond, thereby causing the two double-bonded carbon atoms to be non-equivalent. Regardless, it is seen that squalene presents at least one peak in the range of 131 to 140 ppm (i.e., outside the range of an aromatic compound).

In another embodiment, where information as to the aromatic content (or lack thereof) in the crude oil is independently available, a chemical shift signal, between substantially 125 and 140 ppm, is used to identify the presence of an SBM.

In one embodiment, the double-bonded carbon atom weight fraction (hereinafter referred to as the olefinic content) in a formation fluid (e.g., oil sample) is measured by integrating the area under the $^{13}$C spectral olefinic NMR peaks and dividing that by the area under the $^{13}$C NMR peaks of the spectrum (e.g., all of the $^{13}$C NMR peaks of the spectrum). In another embodiment, the olefinic content in a formation fluid is measured by integrating the area under the spectral curve corresponding to a chemical shift of between about 110 and 150 ppm, or the areas under the spectral curve corresponding to a chemical shift of between about 110 and 120 ppm and 130 and 140 ppm and dividing that by the area under the entire spectral curve for hydrocarbons (e.g., 14 ppm to 150 ppm). As with the proton spectroscopy, if desired, a standard may be added to the sample, and after a $^{13}$C spectral NMR experiment, the area under the olefin peaks or olefinic area is compared to the area under the peak of the standard in order to derive the weight percentage of olefins in the sample.

In one aspect, as with the proton spectroscopy, the olefinic content determined via a $^{13}$C spectral NMR experiment may be converted to a weight percentage of the sample that is SBM by knowing the constituents of the SBM.

In one embodiment, a formation fluid (e.g., oil sample) obtained from a formation is obtained by a sample obtaining tool located in a wellbore (e.g., a wireline tool). The sample is brought uphole and subjected to a $^{13}$C NMR spectral experiment (test). The concentration of contamination of the sample by SBM is then found by determining the olefinic content of the sample via the $^{13}$C NMR spectral test and through knowledge or an estimate of olefinic weight percentage in the SBM.

The methods previously described may be conducted with $^{13}$C NMR spectral equipment located uphole or downhole.

In another embodiment, a formation fluid (e.g., oil sample) obtained from a formation is obtained by a sample obtaining tool located in a wellbore (e.g., a wireline tool). The sample is brought uphole, and a standard is added to the sample which is then subjected to a $^{13}$C NMR spectral experiment (test). The amount of contamination of the sample by SBM is then found by comparing the olefinic content of the sample via the NMR spectral test to the standard content and using that comparison as well as knowledge or an estimate of olefinic weight percentage in the SBM.

According to one aspect, an indication of the olefinic content of the formation fluid found as a result of a $^{13}$C NMR spectral test is used to estimate the amount of contamination of the sample by SBM. In one embodiment, the indication of the olefinic content is obtained by subjecting the sample to a $^{13}$C NMR spectral test and inspecting the peaks in the 110-150 ppm (or 110-120 ppm and 130-140 ppm) portion of the spectrum. In another embodiment, the indication of the olefinic content is obtained by subjecting the sample to an NMR spectral test and inspecting the "internal, adjacent to double-bonded" peak at approximately 34 to 40 ppm. While the "internal, adjacent to double-bonded" peak is not an olefinic peak, it represents the amount of a particular compound that is adjacent an olefin, thereby indicating the presence of an olefin. If a correlation is known for the area under this peak with the expected area under the olefinic peaks, then this peak can be used in lieu of the olefinic peaks in determining the olefinic content and hence the contamination. In one aspect, a correlation may be found by investigating numerous samples with different olefinic contents and comparing the area under the olefin alpha peak with the area under one or more of the olefinic peaks. In another embodiment, a correlation is found by comparing the area under the olefin alpha peak to the known olefin content of an SBM.

In another embodiment, because the $^{13}$C chemical shift of "adjacent to aromatic" is at substantially 21 to 38 ppm, if there are aromatics in the sample, the presence of the aromatics can complicate a determination as to whether a signal relates to an adjacent to double-bonded olefin. Thus, in one embodiment, a chemical shift signal at between substantially 39 and 40 ppm is used to identify "adjacent to double-bonded" olefins present in the sample. In another embodiment, where information as to the "adjacent to aromatic" and/or aromatic content (or lack thereof) in the crude oil is independently available, a chemical shift signal between substantially 34 and 40 ppm, is used to identify the presence of an SBM.

In one embodiment, chemical shift information from both the proton NMR spectrum and the $^{13}$C spectrum may be used together to determine the presence and/or extent of an olefin in a formation fluid. This may be done by looking at different parts of the spectra in order to make determinations and/or in order to confirm determinations.

Figure 6:
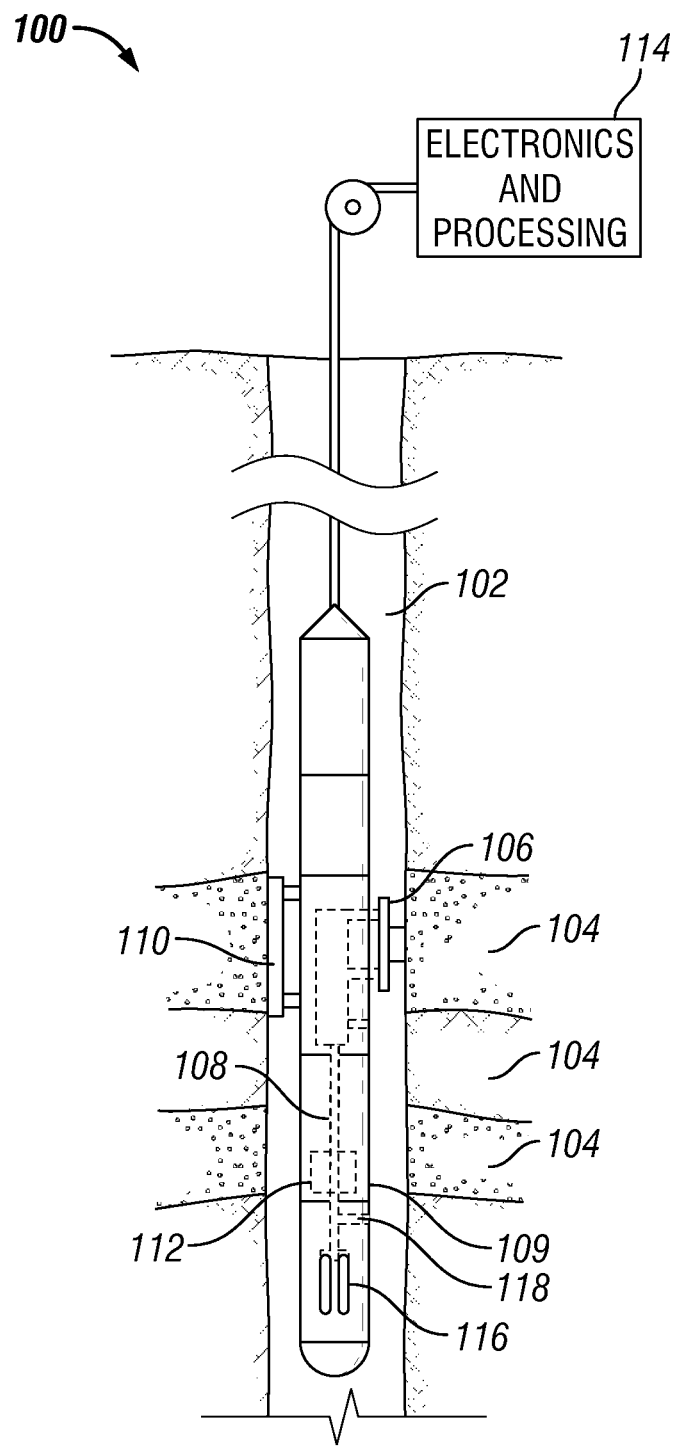
FIG. 6 is a schematic diagram of an apparatus for determining mud contamination of a formation fluid downhole.

Turning to FIG. 6, a schematic diagram shows a wellbore tool 100 for determining mud contamination of a formation fluid. In this example, the wellbore tool 100 is a wireline tool. The wireline tool 100 is disposed within a wellbore 102 that traverses a formation 104. The wireline tool includes 100 a formation fluid testing module, such as the Modular Formation Dynamics Tester™ (MDT) module of Schlumberger. The formation fluid testing module includes a selectively extendable fluid admitting assembly (e.g., probe) 106. This assembly 106 extends into the formation 104 and withdraws formation fluid from the formation 104 (e.g., samples the formation). The fluid flows through the assembly 106 and into a flow line 108 within a housing 109 of the tool 100. A pump module (not shown) is used to withdraw the formation fluid from the formation 104 and pass the fluid through the flow line 108. An optical analyzer (not shown) can be used to conduct optical tests on the fluid within the flow line 108. The wireline tool 102 may also include a selectively extendable tool anchoring member 110 that is arranged to press the probe 106 assembly against the formation 104.

The wireline tool 100 also includes a NMR module 112 for analyzing at least a portion of the fluid in the flow line 108 (e.g., an oil sample). In illustrative embodiments, the NMR module 112 applies a homogeneous static magnetic field to the fluid in the flow line 108 and generates a spectral pulse sequence (e.g., a ninety degree or one hundred eighty degree pulse followed by an acquisition period). In this manner, the NMR module 112 performs a spectral NMR analysis of the fluid within the flow line 108 to obtain a chemical shift spectrum. Further details regarding downhole NMR systems that can perform NMR spectroscopy in a flow line can be found in U.S. Pat. No. 8,471,559, issued on Jun. 25, 2013, and U.S. Patent Application Publication No. 2012/0169334, published on Jul. 5, 2012. Each of these references is incorporated by reference herein in their entireties.

The wireline tool 100 may contain a processor or processors for generating a spectrum from the detected signals and analyzing the spectrum, as described herein. Alternatively or in addition, a processor or processors 114 may be located uphole, and signals may be sent from the wireline tool 100 uphole for processing. The processor may be a programmed computer, a dedicated processor, a system of microprocessors or other circuitry capable of analyzing the NMR data obtained by the NMR module 112 in order to determine the concentration of contamination of the sample.

After the NMR module 112, the formation fluid (e.g., the oil sample) may be pumped out of the flow line 108 and into the wellbore 102 through a port 118. Some of the formation fluid may also be passed to a fluid collection module 116 that includes chambers for collecting fluid samples and retaining samples of the formation fluid for subsequent transport and testing at the surface (e.g., at a testing facility or laboratory).

In illustrative embodiments, the concentration of contamination determined by the NMR module 112 and processor 114 may be reported to an operator or may be used to automatically control whether a fluid sample is kept for storage in the fluid collection module 116 or jettisoned into the wellbore 102 through the port 118. In this manner, samples obtained by the wireline tool 100 may be monitored for contamination and, when a sample containing an "acceptable" concentration of contamination is obtained, the sample may be stored in the fluid collection module 116 and brought uphole for further analysis. The acceptable concentration may be determined relative to a threshold value.

The methods described herein can be implemented by various other wellbore tools and wellbore tool configurations. For example, the methods described herein can be implemented by a wellbore tool that is conveyed by other means, such coiled tubing. Furthermore, the methods described herein can also be applied in logging-while-drilling (LWD) operations, sampling-while-drilling operations, measuring-while-drilling operations, or any other operation where monitoring of formation fluid is performed.

Furthermore, in some embodiments, the methods described herein are performed in a wellbore using a wellbore tool. In other embodiments, the methods described herein are performed at the surface using a laboratory NMR system on formation fluid that has been brought to the surface. Also, the the methods described herein can be used to analyze a variety of different types of formation fluids. In particular, the methods can be used to analyze light oils, heavy oils, biodegraded oils, water washed oils, live oils, dead oils, gases, and water.

There have been described and illustrated herein several embodiments of methods of determining mud contamination of a formation fluid. While particular embodiments and aspects have been described, it is not intended that the disclosure be limited thereto, and it is intended that the claims be as broad in scope as the art will allow and that the specification be read likewise. Thus, while particular ppm ranges have been set forth for olefins and other groups or subgroups, it will be appreciated that the ranges are relative to a standard. In addition it will be appreciated that other ranges could be specified. In addition, it will be appreciated that while multiple olefins are described as being identified, the methods and apparatus may be used to identify a single olefin in an SBM, and if the amount of that olefin is known relative to the SBM itself, the extent of contamination of the formation fluid can be determined. Also, while identification of olefins was described utilizing a proton spectrum and/or a $^{13}$C spectrum, it will be appreciated that other NMR chemical shift spectra could be utilized. It will therefore be appreciated by those skilled in the art that yet other modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method of characterizing a single formation fluid sample, the method comprising:
   subjecting the single sample to a spectral nuclear magnetic resonance (NMR) analysis to obtain a chemical shift spectrum; and
   determining a concentration of synthetic based mud (SBM) contamination within the single sample by identifying an indication of an olefin within the spectrum without reference to another sample.

2. The method according to claim 1, wherein identifying the indication of the olefin comprises locating at least one peak within the spectrum representing the olefin.

3. The method according to claim 2, wherein the spectral NMR analysis detects hydrogen nuclei and the spectrum is a proton NMR spectrum.

4. The method according to claim 3, wherein identifying the indication of the olefin comprises integrating under the at least one peak between about 4.5 and about 6 ppm to obtain an olefin total and dividing the obtained olefin total by a spectrum total obtained by integrating under all peaks in the spectrum.

5. The method according to claim 4, wherein the olefin comprises a plurality of olefins and the at least one peak comprises a plurality of peaks between about 4.5 and about 6 ppm.

6. The method according to claim 3, further comprising:
   adding a standard to the single sample prior to subjecting the single sample to the spectral NMR analysis, wherein identifying the indication of the olefin comprises integrating under the at least one peak between about 4.5 and about 6 ppm to obtain an olefin total and dividing the olefin total by a standard total obtained by integrating under a peak representing the standard.

7. The method according to claim 6, wherein the standard is tetramethylsilane (TMS).

8. The method according to claim 6, wherein the olefin comprises a plurality of olefins and the at least one peak comprises a plurality of peaks between about 4.5 and about 6 ppm.

9. The method according to claim 2, wherein identifying the indication of the olefin comprises locating a peak representing a chemical shift of a compound adjacent an olefin in the sample.

10. The method according to claim 9, wherein the peak representing a $^1$H chemical shift of a compound adjacent a olefin is between about 1.9 and about 2.1 ppm.

11. The method according to 10, further comprising:
    adding a standard to the single sample prior to subjecting the single sample to the spectral NMR analysis, wherein identifying the indication of the olefin comprises integrating under at least one peak between about 1.9 and about 2.1 ppm to obtain an olefin total and dividing the olefin total by a standard total obtained by integrating under a peak representing the standard.

12. The method according to claim 2, wherein the spectral NMR analysis detects carbon nuclei and the spectrum is a $^{13}$C NMR spectrum.

13. The method according to claim 12, wherein the at least one peak is located between about 110 and about 150 ppm within the spectrum.

14. The method according to claim 9, wherein the peak representing the chemical shift of the compound adjacent the olefin is at a chemical shift in a $^{13}$C NMR spectrum located between about 34 and about 40 ppm.

15. The method according to claim 14, wherein the peak representing the chemical shift of the compound adjacent the olefin is at a chemical shift in the $^{13}$C NMR spectrum located between about 39 and about 40 ppm.

16. The method according to claim 1, wherein the concentration of SBM contamination comprises at least one of a hydrogen percentage and a weight percentage.

17. The method according to claim 1, further comprising:
    prior to subjecting the single sample to a spectral NMR analysis, locating a tool downhole in a formation and obtaining the single sample.

18. The method according to claim 17, wherein subjecting the sample to a spectral NMR analysis comprises conducting the spectral NMR analysis downhole.

19. The method according to claim 18, further comprising:
    jettisoning the single sample downhole based on the concentration of SBM contamination.

20. The method according to claim 18, further comprising:
    storing the single sample in said tool based on the concentration of SBM contamination.

21. An apparatus for characterizing a single formation fluid sample, the apparatus comprising:
    a nuclear magnetic resonance (NMR) module for conducting a spectral NMR analysis of the single sample; and
    a processor configured to determine synthetic based mud contamination of the single formation fluid sample using the spectral NMR analysis without reference to another sample.

22. The apparatus according to claim 21, wherein the NMR module is part of a wellbore tool and the wellbore tool is configured to withdraw fluid from a formation.

23. An apparatus according to claim 22, wherein the processor is located uphole.

24. An apparatus according to claim 22, wherein the wellbore tool includes a chamber for storing the single sample.

* * * * *